(12) United States Patent
Addison et al.

(10) Patent No.: US 11,638,606 B2
(45) Date of Patent: May 2, 2023

(54) BIPOLAR ELECTROSURGICAL PLEURA SEALING DEVICE, SYSTEM, AND METHOD OF OPERATING SAME

(71) Applicant: Bard Peripheral Vascular, Inc., Franklin Lakes, NJ (US)

(72) Inventors: Jordan P. Addison, Chandler, AZ (US); Koltin K. Glaspie, Chandler, AZ (US); Heather A. Storm, Phoenix, AZ (US); Ryan Striedel, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 429 days.

(21) Appl. No.: 16/849,247

(22) Filed: Apr. 15, 2020

(65) Prior Publication Data

US 2021/0322091 A1    Oct. 21, 2021

(51) Int. Cl.
*A61B 18/14* (2006.01)
*A61B 18/12* (2006.01)
*A61B 10/02* (2006.01)
*A61B 18/00* (2006.01)

(52) U.S. Cl.
CPC ...... *A61B 18/1477* (2013.01); *A61B 10/0275* (2013.01); *A61B 18/1206* (2013.01); *A61B 2018/0063* (2013.01); *A61B 2018/00083* (2013.01); *A61B 2018/00214* (2013.01); *A61B 2018/00541* (2013.01); *A61B 2018/126* (2013.01)

(58) Field of Classification Search
CPC ......... A61B 2018/00083; A61B 2018/000214; A61B 2018/00267; A61B 2018/00541; A61B 2018/0063; A61B 2018/126; A61B 18/1206; A61B 18/1477
See application file for complete search history.

(56) References Cited

U.S. PATENT DOCUMENTS

| | | | |
|---|---|---|---|
| 5,085,659 A | 2/1992 | Rydell | |
| 5,947,964 A | 9/1999 | Eggers et al. | |
| 5,972,026 A * | 10/1999 | Laufer | A61B 18/00 606/41 |
| 6,315,778 B1 * | 11/2001 | Gambale | A61B 18/1492 606/41 |
| 6,488,673 B1 | 12/2002 | Laufer et al. | |
| 6,529,756 B1 * | 3/2003 | Phan | A61B 18/1492 606/49 |

(Continued)

*Primary Examiner* — Michael F Peffley
(74) *Attorney, Agent, or Firm* — Dinsmore & Shohl LLP

(57) ABSTRACT

A bipolar electrosurgical pleura sealing device includes an electrosurgical probe assembly having a coaxial arrangement that includes an inner stylet, a first intermediate cannula, a second intermediate cannula, and an outer cannula, having appropriate insulation. A first mesh electrode connects to and extends between a distal end portion of the inner stylet and a distal end of the first intermediate cannula, and is movable between a first extended position and a first retracted position by an axial movement of the inner stylet and/or the first intermediate cannula. A second mesh electrode connects to and extends between a distal end of the second intermediate cannula and a distal end of the outer cannula, and is movable between a second extended position and a second retracted position by an axial movement of the second intermediate cannula and/or the outer cannula.

20 Claims, 7 Drawing Sheets

(56) References Cited

U.S. PATENT DOCUMENTS

| | | | |
|---|---|---|---|
| 6,770,070 | B1 | 8/2004 | Balbierz |
| 7,022,088 | B2 | 4/2006 | Keast et al. |
| 7,524,318 | B2 | 4/2009 | Young et al. |
| 7,628,789 | B2 | 12/2009 | Soltesz et al. |
| 7,945,332 | B2 | 5/2011 | Schechter |
| 8,007,495 | B2 * | 8/2011 | McDaniel ........... A61B 18/1492 606/41 |
| 8,147,483 | B2 | 4/2012 | Tan |
| 8,249,685 | B2 * | 8/2012 | Falwell ............... A61B 18/1492 606/41 |
| 8,273,051 | B2 | 9/2012 | Tanaka et al. |
| 8,454,596 | B2 * | 6/2013 | Ma ...................... A61B 18/1492 606/41 |
| 8,496,655 | B2 * | 7/2013 | Epp ........................ A61B 18/14 606/45 |
| 8,551,082 | B2 * | 10/2013 | Strul ................... A61B 18/1206 606/34 |
| 8,628,521 | B2 | 1/2014 | Tan |
| 8,734,362 | B2 | 5/2014 | Boyle, Jr. |
| 8,945,116 | B2 * | 2/2015 | MacAdam .......... A61B 18/1492 606/41 |
| 9,259,265 | B2 | 2/2016 | Harris et al. |
| 9,370,398 | B2 | 6/2016 | Ladtkow et al. |
| 9,901,393 | B2 | 2/2018 | Sunenshine et al. |
| 9,974,524 | B2 | 5/2018 | Frushour et al. |
| 2003/0109802 | A1 | 6/2003 | Laeseke et al. |
| 2009/0124927 | A1 | 5/2009 | Chin et al. |
| 2011/0184313 | A1 | 7/2011 | Gianchandani et al. |
| 2012/0053485 | A1 | 3/2012 | Bloom |
| 2015/0057570 | A1 | 2/2015 | Chin et al. |
| 2016/0015448 | A1 | 1/2016 | Longoria et al. |
| 2019/0000849 | A1 | 1/2019 | Greminger et al. |
| 2019/0125435 | A1 | 5/2019 | Dickhans et al. |
| 2022/0087739 | A1 * | 3/2022 | Palushi .................. A61B 5/062 |

\* cited by examiner

BIPOLAR ELECTROSURGICAL PLEURA SEALING DEVICE, SYSTEM, AND METHOD OF OPERATING SAME

CROSS-REFERENCE TO RELATED APPLICATIONS

None.

TECHNICAL FIELD

The present invention relates to a lung access procedure, such as a lung biopsy, and, more particularly, to a bipolar electrosurgical pleura sealing device, system, and method of operating same, for use in a lung access procedure to aid in preventing pneumothorax.

BACKGROUND ART

Pneumothorax is a problematic complication of the lung biopsy procedure where air or fluid is allowed to pass into the pleural space as a result of the puncture of the parietal pleura and visceral pleura. Pneumothorax and, more so, pneumothorax requiring chest tube placement, are significant concerns for clinicians performing, and patients undergoing, percutaneous lung biopsies. The incidence of pneumothorax in patients undergoing percutaneous lung biopsy has been reported to be anywhere from 9-54%, with an average of around 15%. On average, 6.6% of all percutaneous lung biopsies result in pneumothorax requiring a chest tube to be placed, which results in an average hospital stay of 2.7 days.

Factors that increase the risk of pneumothorax include increased patient age, obstructive lung disease, increased depth of a lesion, multiple pleural passes, increased time that an access needle lies across the pleura, and traversal of a fissure. Pneumothorax may occur during or immediately after the procedure, which is why typically a CT scan of the region is performed following removal of the needle. Other, less common, complications of percutaneous lung biopsy include hemoptysis (coughing up blood), hemothorax (a type of pleural effusion in which blood accumulates in the pleural cavity), infection, and air embolism.

What is needed in the art is a bipolar electrosurgical pleura sealing device, system, and method of operating same, for use in a lung access procedure to aid in preventing pneumothorax.

SUMMARY OF INVENTION

The present invention provides a bipolar electrosurgical pleura sealing device, system, and method of operating same, for use in a lung access procedure to aid in preventing pneumothorax.

The invention, in one form, is directed to a bipolar electrosurgical pleura sealing device that includes an electrosurgical probe assembly having a coaxial arrangement. The electrosurgical probe assembly includes an inner stylet having a distal end portion with a piercing tip, a first intermediate cannula having a first distal end, a second intermediate cannula having a second distal end, and an outer cannula having a third distal end. The inner stylet is electrically insulated from the first intermediate cannula. The first intermediate cannula is electrically insulated from the second intermediate cannula. The second intermediate cannula is electrically insulated from the outer cannula. A first mesh electrode is connected to and extends between the distal end portion of the inner stylet and the first distal end of the first intermediate cannula. The first mesh electrode is configured to have a first extended position that defines a first collapsed state and a first retracted position that defines a first expanded state. The first mesh electrode is configured to move between the first extended position and the first retracted position by an axial movement of at least one of the inner stylet and the first intermediate cannula. A second mesh electrode is connected to and extends between the second distal end of the second intermediate cannula and the third distal end of the outer cannula. The second mesh electrode is configured to have a second extended position that defines a second collapsed state and a second retracted position that defines a second expanded state. The second mesh electrode is configured to move between the second extended position and the second retracted position by an axial movement of at least one of the second intermediate cannula and the outer cannula.

The invention, in another form, is directed to a bipolar electrosurgical pleura sealing system. The system includes a signal generator having a first electrical port and a second electrical port. The signal generator is configured to generate an output signal. An electrosurgical probe assembly has a coaxial arrangement that includes an inner stylet having a distal end portion with a piercing tip, a first intermediate cannula having a first distal end, a second intermediate cannula having a second distal end, and an outer cannula having a third distal end. The inner stylet is electrically insulated from the first intermediate cannula, the first intermediate cannula is electrically insulated from the second intermediate cannula, and the second intermediate cannula is electrically insulated from the outer cannula. A first mesh electrode is coupled in electrical communication with the first electrical port of the signal generator. The first mesh electrode is connected to and extends between the distal end portion of the inner stylet and the first distal end of the first intermediate cannula. The first mesh electrode is configured to have a first extended position that defines a first collapsed state and a first retracted position that defines a first expanded state. The first mesh electrode is configured to move between the first extended position and the first retracted position by an axial movement of at least one of the inner stylet and the first intermediate cannula. A second mesh electrode is coupled in electrical communication with the second electrical port of the signal generator. The second mesh electrode is connected to and extends between the second distal end of the second intermediate cannula and the third distal end of the outer cannula. The second mesh electrode is configured to have a second extended position that defines a second collapsed state and a second retracted position that defines a second expanded state. The second mesh electrode is configured to move between the second extended position and the second retracted position by an axial movement of at least one of the second intermediate cannula and the outer cannula.

The invention, in another form, is directed to a method of operating a bipolar electrosurgical pleura sealing system, including providing a bipolar electrosurgical pleura sealing device that has an electrosurgical probe assembly to a first mesh electrode and a second mesh electrode, each of the first mesh electrode and the second mesh electrode being coupled in electrical communication with a signal generator, the first mesh electrode being movable between a first extended position that defines a first collapsed state and a first retracted position that defines a first expanded state, and the second mesh electrode being movable between a second extended position that defines a second collapsed state and a second retracted position that defines a second expanded state; inserting the bipolar electrosurgical pleura sealing device along an access path in a subject; operating the electrosurgical probe assembly to deploy the first mesh electrode to the first expanded state and to deploy the second mesh electrode to the second expanded state, so as to capture tissue between the first mesh electrode and the second mesh electrode; and activating a signal generator to generate an output signal that energizes the first mesh electrode and the second mesh electrode to heat the tissue between the first mesh electrode and the second mesh electrode.

An advantage of the present invention is that the pair of mesh electrodes may be used to both compress the pleural layers by mechanical compression, and to also electrically fuse the pleural layers at a region surrounding the access opening in the subject.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
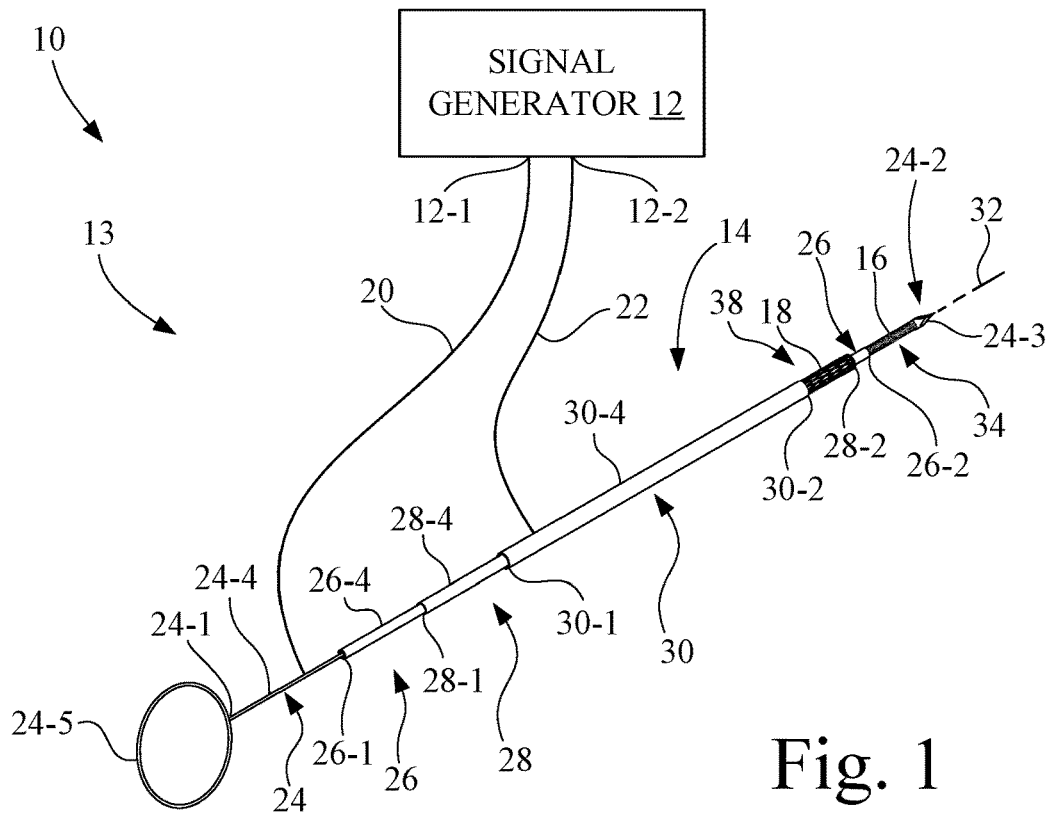
FIG. 1 is a combined block diagram and perspective view of a bipolar electrosurgical pleura sealing system in accordance with the present invention, showing a bipolar electrosurgical pleura sealing device having an electrosurgical probe assembly that carries proximal and distal mesh electrodes, and showings the proximal and distal mesh electrodes in their respective collapsed state.
Figure 2:
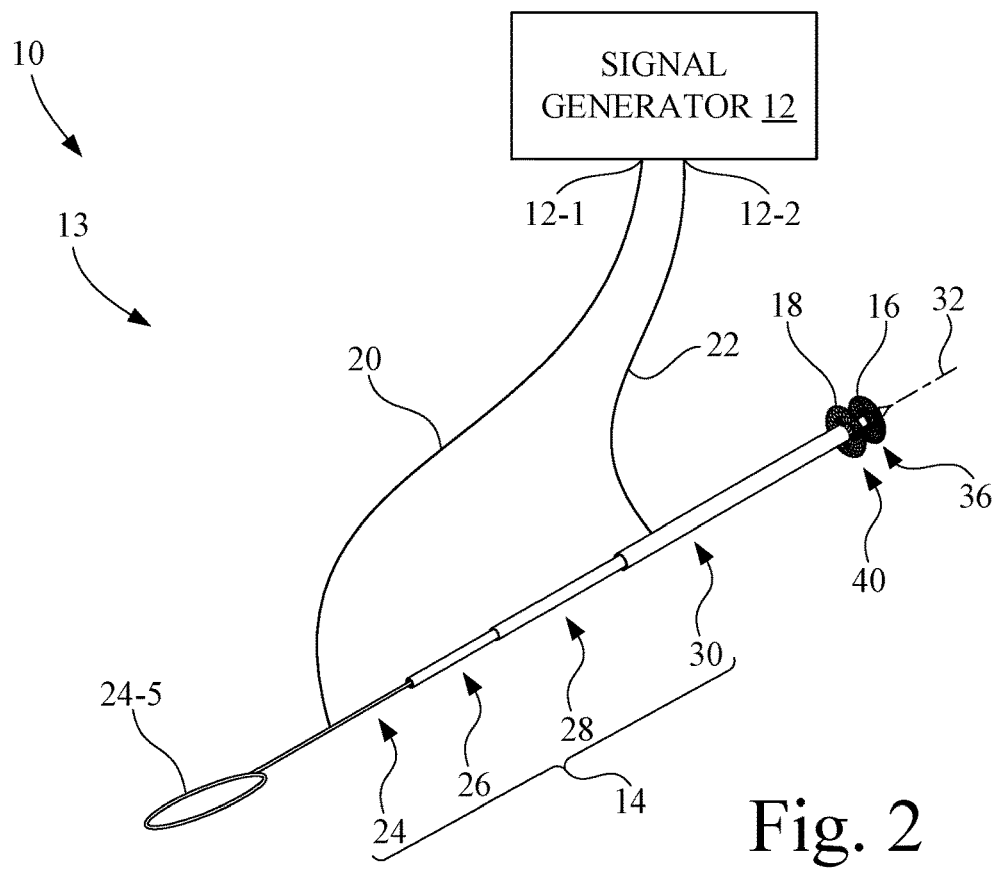
FIG. 2 is a combined block diagram and perspective view of the bipolar electrosurgical pleura sealing system of FIG. 1, showing the bipolar electrosurgical pleura sealing device with the proximal and distal mesh electrodes in their respective expanded state.

Referring now to the drawings, and more particularly to FIGS. 1 and 2, there is shown a bipolar electrosurgical pleura sealing system 10 that includes a signal generator 12 and a bipolar electrosurgical pleura sealing device 13. Bipolar electrosurgical pleura sealing device 13 includes an electrosurgical probe assembly 14, a distal mesh electrode 16, and a proximal mesh electrode 18. The combination of distal mesh electrode 16 and proximal mesh electrode 18 forms a bipolar electrode arrangement.

FIG. 1 shows a pre-deployment position of bipolar electrosurgical pleura sealing device 13, which includes electrosurgical probe assembly 14, distal mesh electrode 16, and proximal mesh electrode 18. Each of distal mesh electrode 16 and proximal mesh electrode 18 individually may be both longitudinally extended and radially retracted to a pre-deployment position by manipulation of components of electrosurgical probe assembly 14.

FIG. 2 shows a deployment position of bipolar electrosurgical pleura sealing device 13. Each of distal mesh electrode 16 and proximal mesh electrode 18 individually may be both longitudinally retracted and radially expanded to a deployment position by manipulation of components of electrosurgical probe assembly 14. In other words, when each of distal mesh electrode 16 and proximal mesh electrode 18 is longitudinally retracted, then each of distal mesh electrode 16 and proximal mesh electrode 18 is radially expanded.

Signal generator 12, e.g., a bipolar electrosurgical generator, is configured to generate an output signal. Signal generator 12 may be, for example, a radio frequency signal generator, and the output signal may be a radio frequency signal. For example, the radio frequency signal may have a frequency in a range of 300 kHz and 600 kHz. Also, the radio frequency signal may be a pulsed waveform, e.g., an on/off signal, that may help to prevent tissue sticking to distal mesh electrode 16 and proximal mesh electrode 18. In a more particular example, the radio frequency signal has a frequency of, or about, 492 kHz.

Signal generator 12 has a first electrical port 12-1 and a second electrical port 12-2, wherein each of first electrical port 12-1 and a second electrical port 12-2 is electrically coupled to bipolar electrosurgical pleura sealing device 13. More particularly, first electrical port 12-1 and a second electrical port 12-2 are electrically coupled to distal mesh electrode 16 and proximal mesh electrode 18, respectively.

A first electrical lead 20, e.g., an insulated electrical conductor, has opposed ends that are respectively electrically coupled to distal mesh electrode 16 and to first electrical port 12-1 of signal generator 12. First electrical lead 20 may be directly connected to each of distal mesh electrode 16 and first electrical port 12-1 of signal generator 12. Alternatively, first electrical lead 20 may be indirectly connected to distal mesh electrode 16 via a conductive, e.g., metal, portion of electrosurgical probe assembly 14.

A second electrical lead 22, e.g., an insulated electrical conductor, has opposed ends that are respectively electrically coupled to proximal mesh electrode 18 and to second electrical port 12-2 of signal generator 12. Second electrical lead 22 may be directly connected to each of proximal mesh electrode 18 and second electrical port 12-2 of signal generator 12. Alternatively, second electrical lead 22 may be indirectly connected to proximal mesh electrode 18 via a conductive, e.g., metal, portion of electrosurgical probe assembly 14.

Figure 3:
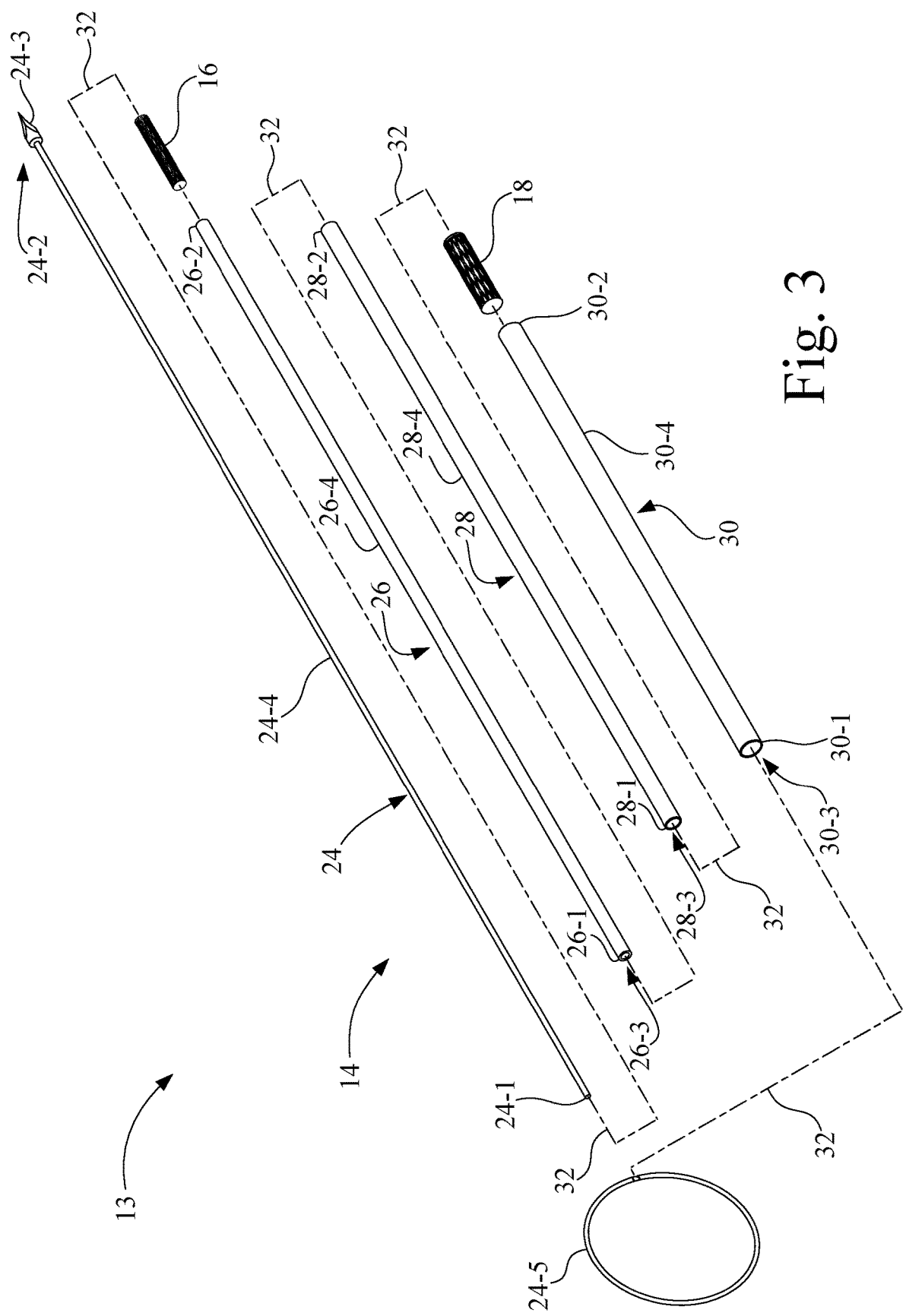
FIG. 3 is an exploded perspective view of the bipolar electrosurgical pleura sealing device of FIG. 1.

Referring also to FIG. 3, electrosurgical probe assembly 14 of bipolar electrosurgical pleura sealing device 13 is configured as a coaxial arrangement that includes an inner stylet 24, a first intermediate cannula 26, a second intermediate cannula 28, and an outer cannula 30 arranged along a longitudinal axis 32.

Inner stylet 24 has a stylet proximal end 24-1, a distal end portion 24-2 with a piercing tip 24-3, a stylet outer surface 24-4, and a handle ring 24-5 connected (e.g., threadably) to stylet proximal end 24-1. First intermediate cannula 26 has a first proximal end 26-1, a first distal end 26-2, a first lumen 26-3, and a first outer surface 26-4. Second intermediate cannula 28 has a second proximal end 28-1, a second distal end 28-2, a second lumen 28-3, a second outer surface 28-4. Outer cannula 30 has a third proximal end 30-1, a third distal end 30-2, a third lumen 30-3, and a third outer surface 30-4. In the coaxial arrangement of electrosurgical probe assembly 14, inner stylet 24 is electrically insulated from first intermediate cannula 26, first intermediate cannula 26 is electrically insulated from second intermediate cannula 28, and second intermediate cannula 28 is electrically insulated from outer cannula 30.

The electrical insulated separation of inner stylet 24 and first intermediate cannula 26 may be achieved by interposing an insulation material between inner stylet 24 and first intermediate cannula 26. For example, inner stylet 24 and first intermediate cannula 26 may be made of metal (e.g., a stainless steel tube), wherein stylet outer surface 24-4 of inner stylet 24 and/or an interior surface of first lumen 26-3 of first intermediate cannula 26 may have, or may be, an insulation coating. Each insulation coating may be, for example, at least one of ceramic, rubber, and plastic.

Likewise, the electrical insulated separation of first intermediate cannula 26 and second intermediate cannula 28 may be achieved by interposing an insulation material between first intermediate cannula 26 and second intermediate cannula 28. For example, second intermediate cannula 28 may be made of metal (e.g., a stainless steel tube), wherein first outer surface 26-4 of first intermediate cannula 26 and/or an interior surface of second lumen 28-3 of second intermediate cannula 28 may have, or may be, an insulation coating. Each insulation coating may be, for example, at least one of ceramic, rubber, and plastic.

Likewise, the electrical insulated separation of second intermediate cannula 28 and outer cannula 30 may be achieved by interposing an insulation material between second intermediate cannula 28 and outer cannula 30. For example, outer cannula 30 may be made of metal (e.g., a stainless steel tube), wherein second outer surface 28-4 of second intermediate cannula 28 and/or an interior surface of third lumen 30-3 of outer cannula 30 may have, or may be, an insulation coating. Each insulation coating may be, for example, at least one of ceramic, rubber, and plastic.

In one embodiment, for example, each of inner stylet 24, first intermediate cannula 26, second intermediate cannula 28, and outer cannula 30 may have an insulation coating over the respective interior and outer surfaces. Each insulation coating may be, for example, at least one of ceramic, rubber, and plastic. Alternatively, first intermediate cannula 26 and/or second intermediate cannula 28 may be made of an electrically non-conductive material, such as an electrically non-conductive polymer tube.

In another embodiment, for example, only first intermediate cannula 26 and second intermediate cannula 28 have an insulation coating, such as for example, wherein first intermediate cannula 26 may have a first insulation coating over respective interior and outer surfaces (i.e., both over the interior surface of first lumen 26-3 and over first outer surface 26-4), and second intermediate cannula 28 may have a second insulation coating over respective interior and outer surfaces (i.e., both over the interior surface of second lumen 28-3 and over second outer surface 28-4). Each of the first insulation coating and the second insulation coating may be at least one of ceramic, rubber, and plastic.

Distal mesh electrode 16 is coupled in electrical communication with first electrical port 12-1 of signal generator 12. Distal mesh electrode 16 is connected to and extends between the distal end portion 24-2 of inner stylet 24 and first distal end 26-2 of first intermediate cannula 26. Distal mesh electrode 16 may be, for example, a cylindrically shaped wire mesh, e.g., having crisscrossed wires or members, which is radially expandable when the length of the cylindrically shaped wire mesh is shortened. Distal mesh electrode 16 may be made from a biocompatible metal, such as stainless steel, nitinol, etc. Also, distal mesh electrode 16 may have a non-stick coating, e.g., PTFE, on the electrode wires to prevent charring/sticking.

Figure 4:
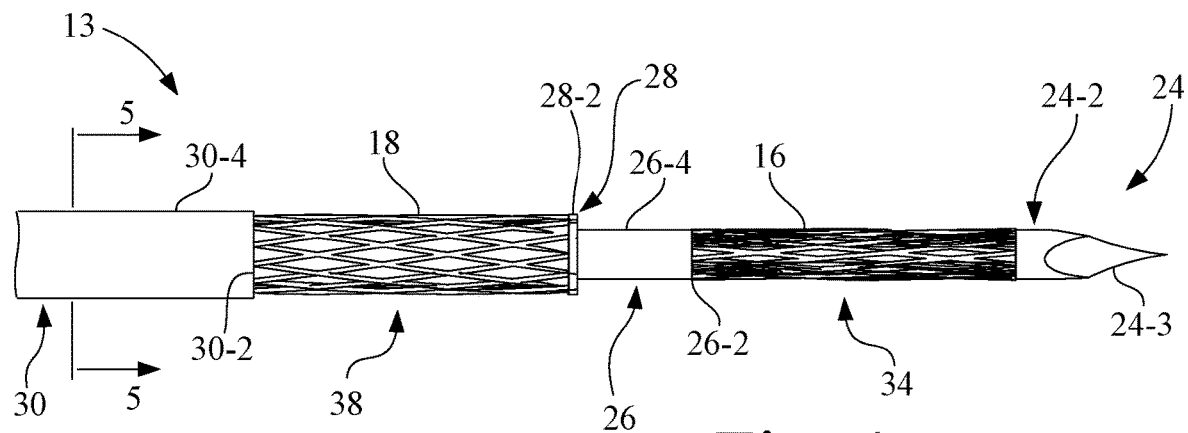
FIG. 4 is an enlarged side view of a distal portion of the bipolar electrosurgical pleura sealing device of FIG. 1, showing the proximal and distal mesh electrodes in their respective collapsed state.
Figure 5:
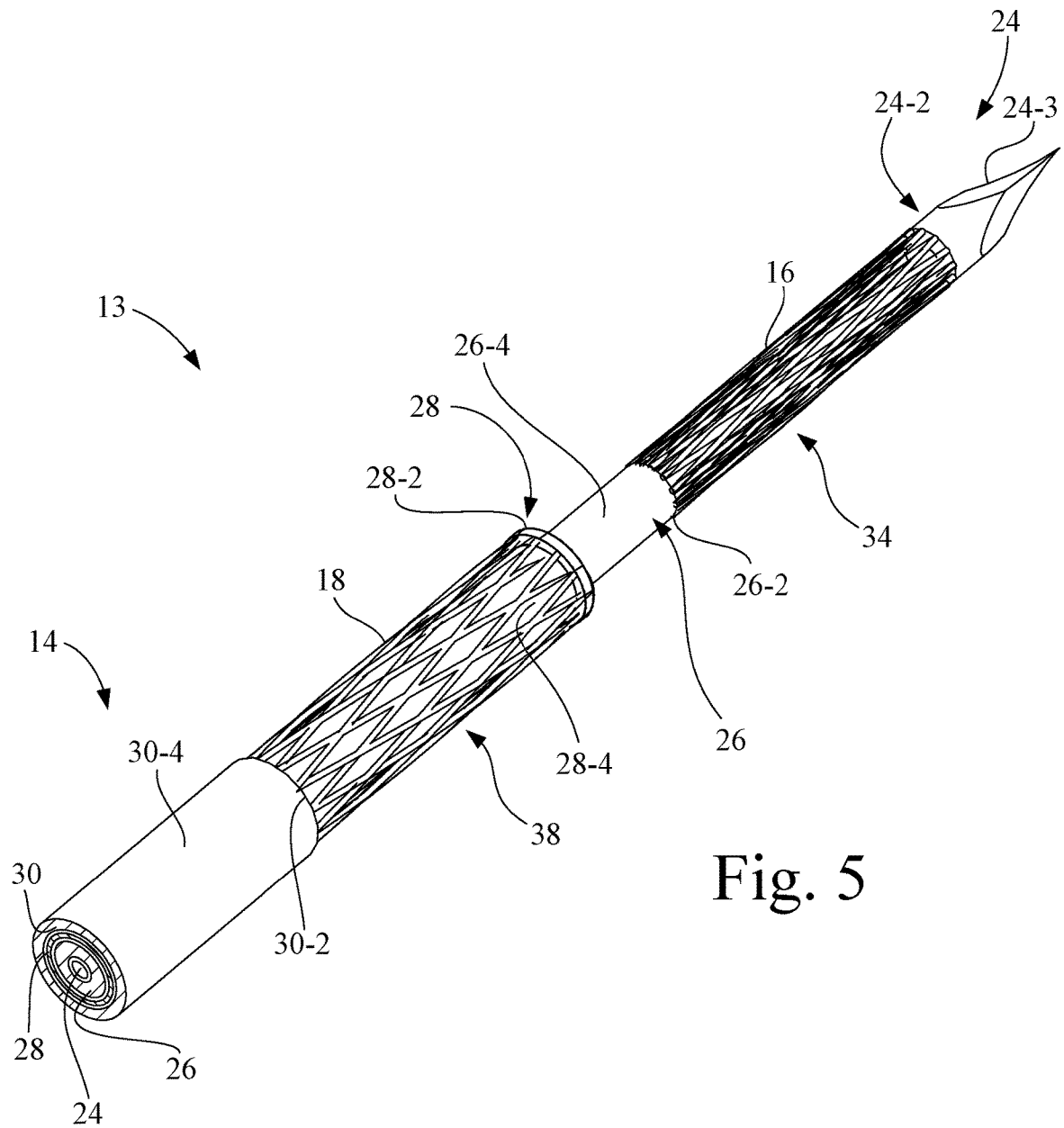
FIG. 5 is a section perspective view of the enlarged distal portion of the bipolar electrosurgical pleura sealing device of FIG. 4, taken along line 5-5 of FIG. 4.
Figure 6:
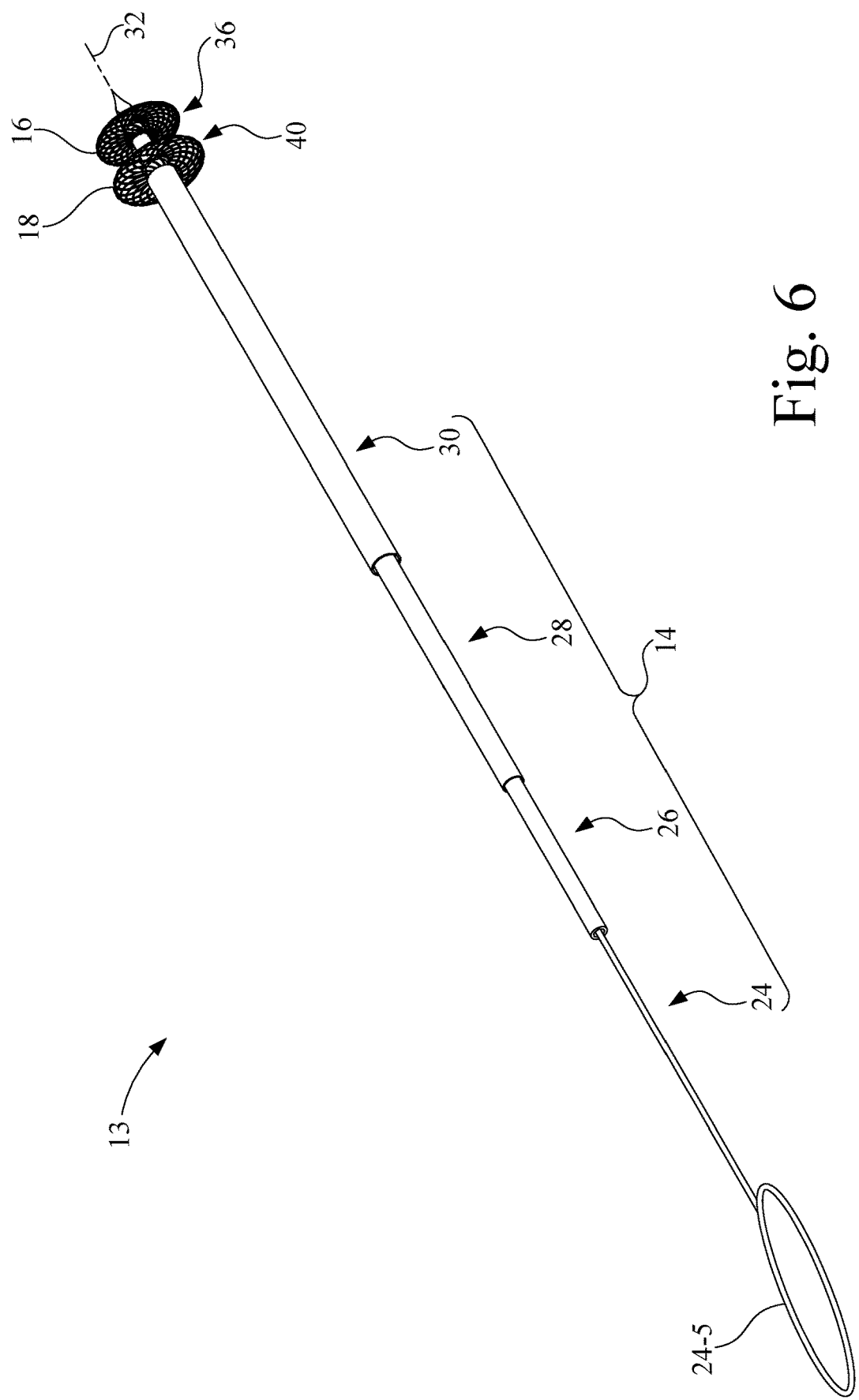
FIG. 6 is an enlarged perspective view of the bipolar electrosurgical pleura sealing device of FIG. 2, showing the proximal and distal mesh electrodes in their respective expanded state.
Figure 7:
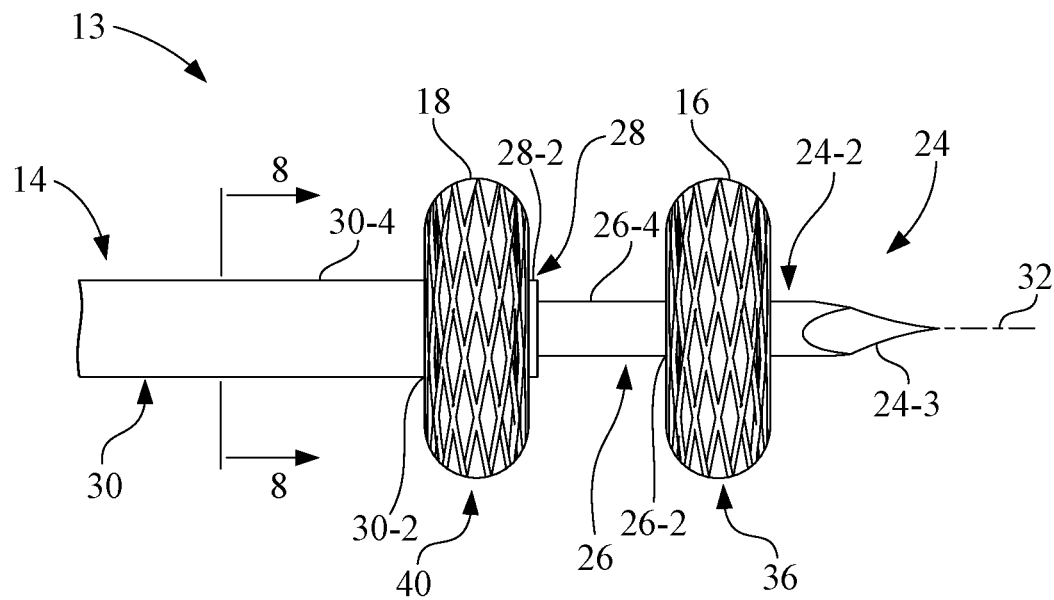
FIG. 7 is a further enlarged side view of a distal portion of the bipolar electrosurgical pleura sealing device of FIGS. 2 and 6, showing the proximal and distal mesh electrodes in their respective expanded (deployed) state.
Figure 8:
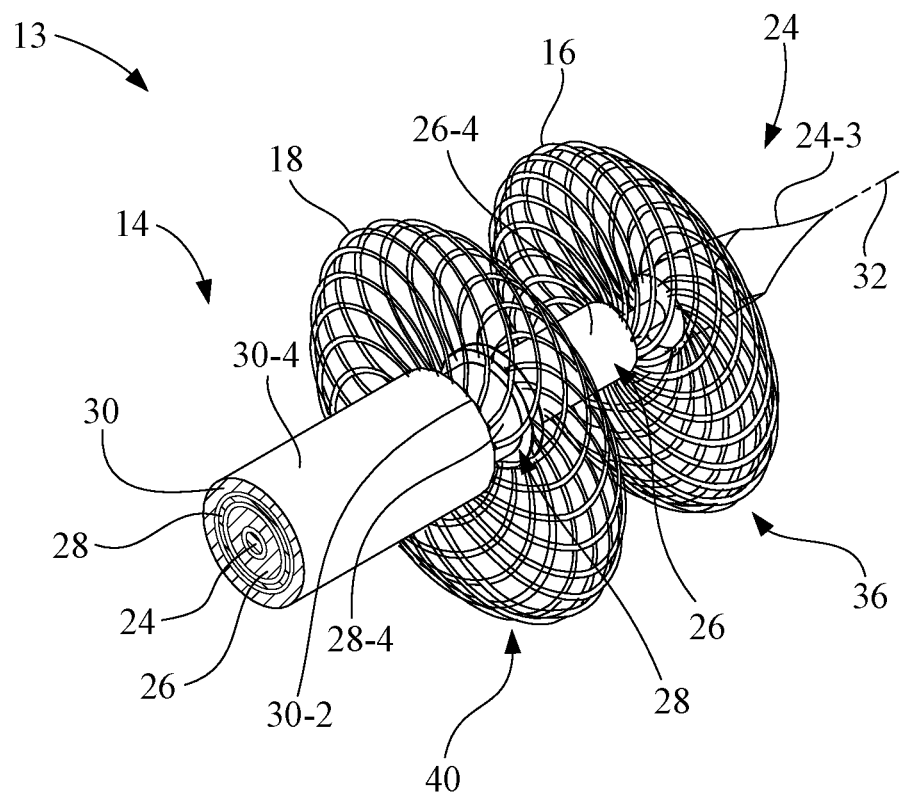
FIG. 8 is a section perspective view of the enlarged distal portion of the bipolar electrosurgical pleura sealing device of FIG. 7, taken along line 8-8 of FIG. 7.

Distal mesh electrode 16 is configured to have a first extended position 34 that defines a collapsed state 34 (see FIGS. 1, 4, and 5) and a first retracted position 36 that defines an expanded state 36 (see FIGS. 2 and 6-9). It is noted that, for convenience and ease of illustration, element no. 34 will be used when describing either, or both, of first extended position 34 and/or collapsed state 34; and, element no. 36 will be used when describing either, or both, of first retracted position 36 and/or expanded state 36.

When distal mesh electrode 16 is in first extended position 34, then also distal mesh electrode 16 is longitudinally extended and radially retracted to collapsed state 34. When distal mesh electrode 16 is in first retracted position 36, then also distal mesh electrode 16 is in expanded state 36. Distal mesh electrode 16 is configured to move between first extended position 34 and first retracted position 36 by an axial movement of at least one of inner stylet 24 and first intermediate cannula 26.

Proximal mesh electrode 18 is coupled in electrical communication with second electrical port 12-2 of signal generator 12. Proximal mesh electrode 18 is connected to and extends between second distal end 28-2 of second intermediate cannula 28 and the third distal end 30-2 of outer cannula 30. Proximal mesh electrode 18 may be, for example, a cylindrically shaped wire mesh, e.g., having crisscrossed wires or members, which is radially expandable when the length of the cylindrically shaped wire mesh is shortened. Proximal mesh electrode 18 may be made from a biocompatible metal, such as stainless steel, nitinol, etc. Also, proximal mesh electrode 18 may have a non-stick coating, e.g., PTFE, on the electrode wires to prevent charring/sticking.

Proximal mesh electrode 18 is configured to have a second extended position 38 that defines a collapsed state 38 (see FIGS. 1, 4, and 5) and a second retracted position 40 that defines an expanded state 40 (see FIGS. 2 and 6-9). It is noted that, for convenience and ease of illustration, element no. 38 will be used when describing either, or both, of second extended position 38 and/or collapsed state 38; and, element no. 40 will be used when describing either, or both, of second retracted position 40 and/or expanded state 40.

When proximal mesh electrode 18 is in the second extended position 38, then also proximal mesh electrode 18 is longitudinally extended and radially retracted to the collapsed state 38. When proximal mesh electrode 18 is in the second retracted position 40, then also proximal mesh electrode 18 is longitudinally retracted and radially extended to the expanded state 40. Proximal mesh electrode 18 is configured to move between second extended position 38 and second retracted position 40 by an axial movement of at least one of second intermediate cannula 28 and outer cannula 30.

Distal mesh electrode 16 and proximal mesh electrode 18 form a bipolar electrode arrangement, wherein one of distal mesh electrode 16 and proximal mesh electrode 18 may be designated as a primary electrode, and the other of distal mesh electrode 16 and proximal mesh electrode 18 may be designated as a return electrode.

Figure 9:
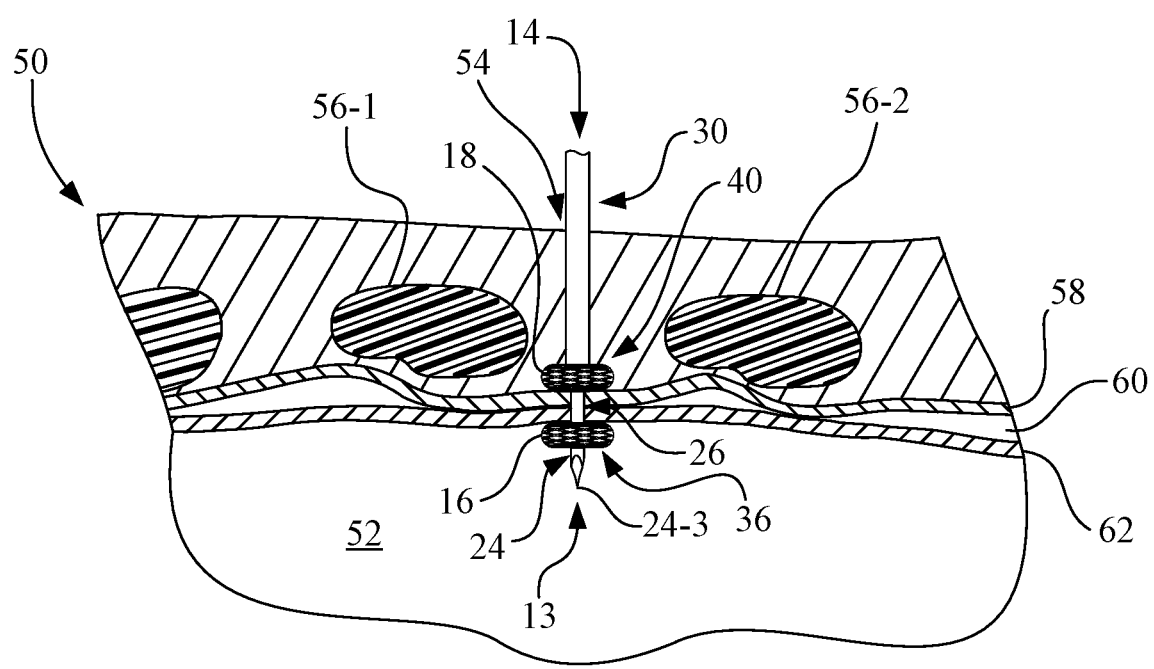
FIG. 9 pictorially depicts a section view of a portion of a chest wall and lung of a subject, and shows a side view of the bipolar electrosurgical pleura sealing device having the electrosurgical probe assembly, proximal mesh electrode, and distal mesh electrode, with the proximal mesh electrode and the distal mesh electrode in their respective expanded (deployed) state on opposite sides of the pleural layers.

Referring to FIG. 9, there is depicted a portion of a chest wall 50 and lung 52 of a subject, such as a patient, cadaver, or animal. Electrosurgical probe assembly 14 is used to form an access opening 54 to the interior of lung 52. For example, access opening 54 may be formed between adjacent ribs 56-1, 56-2 in the rib cage of chest wall 50 by advancing piercing tip 24-3 of electrosurgical probe assembly 14 into the subject. Access opening 54 extends though the parietal pleura 58, the pleural space 60, and the visceral pleura 62 to provide access to the interior of the lung 52. Collectively, parietal pleura 58 and visceral pleura 62 are referred to herein as the pleural layers 58, 62.

Referring to FIGS. 1, 2, and 9, distal mesh electrode 16 is configured to move between first extended position (collapsed state) 34 and first retracted position (expanded state) 36 by an axial movement of at least one of inner stylet 24 and first intermediate cannula 26. For example, referring to FIGS. 1 and 2, distal mesh electrode 16 may be moved from first extended position (collapsed state) 34 to first retracted position (expanded state) 36 by retracting (e.g., pulling) inner stylet 24 relative to first intermediate cannula 26 so as to expand distal mesh electrode 16.

Likewise, referring to FIGS. 1, 2, and 9, proximal mesh electrode 18 is moved between second extended position (collapsed state) 38 and second retracted position (expanded state) 40 by an axial movement of at least one of second intermediate cannula 28 and outer cannula 30. For example, referring to FIGS. 1 and 2, proximal mesh electrode 18 may be moved from second extended position (collapsed state) 38 to second retracted position (expanded state) 40 by retracting, e.g., pulling, second intermediate cannula 28 relative to outer cannula 30 to expand proximal mesh electrode 18.

FIG. 9 shows the deployed arrangement of bipolar electrosurgical pleura sealing device 13 situated in access opening 54, with distal mesh electrode 16 in the first retracted position (expanded state) 36 being located distal to (and adjacent), i.e., below, the visceral pleura 62, and with proximal mesh electrode 18 in the second retracted position (expanded state) 40 being located proximal to (and adjacent), i.e., above, parietal pleura 58. The location of distal mesh electrode 16 and proximal mesh electrode 18 relative to the pleural layers 58, 62 may be determined and/or confirmed, using an imaging system, such as for example, ultrasound imaging or X-ray imaging, if desired.

Referring to FIGS. 2 and 9, with distal mesh electrode 16 and proximal mesh electrode 18 in their respective expanded states 36, 40, then by the act of further retracting inner stylet 24 relative to outer canula 30, distal mesh electrode 16 is moved, e.g., slid, proximally toward proximal mesh electrode 18 so as to move the pleural layers 58, 62 into contact, and into compression if desired. Stated differently, one or both of distal mesh electrode 16 and proximal mesh electrode 18 may slide relative to the other so as to generate compression of the tissues, e.g., the pleural layers 58, 62, to be sealed.

Thereafter, referring to FIGS. 1, 2, and 9, signal generator 12, e.g., a bipolar electrosurgical generator, may then be activated to supply the radio frequency signal to the bipolar electrode arrangement formed by distal mesh electrode 16 and proximal mesh electrode 18. The radio frequency signal may have a frequency, for example, in a range of 300 kHz and 600 kHz. In a more particular example, the radio frequency signal may have a frequency of, or about, 492 kHz.

In the present embodiment, one of distal mesh electrode 16 and proximal mesh electrode 18 is (i.e., serves as) a primary electrode and the other of distal mesh electrode 16 and proximal mesh electrode 18 is (i.e., serves as) a return electrode. The radio frequency signal generated by signal generator 12 travels through the tissue (e.g., plural layers 58, 62; see FIG. 9) that surrounds access opening 54 and captured between distal mesh electrode 16 and proximal mesh electrode 18, so as to heat the tissue therebetween, which denatures the proteins in the tissue to in turn bond the plural layers 58, 62 together.

Figure 10:
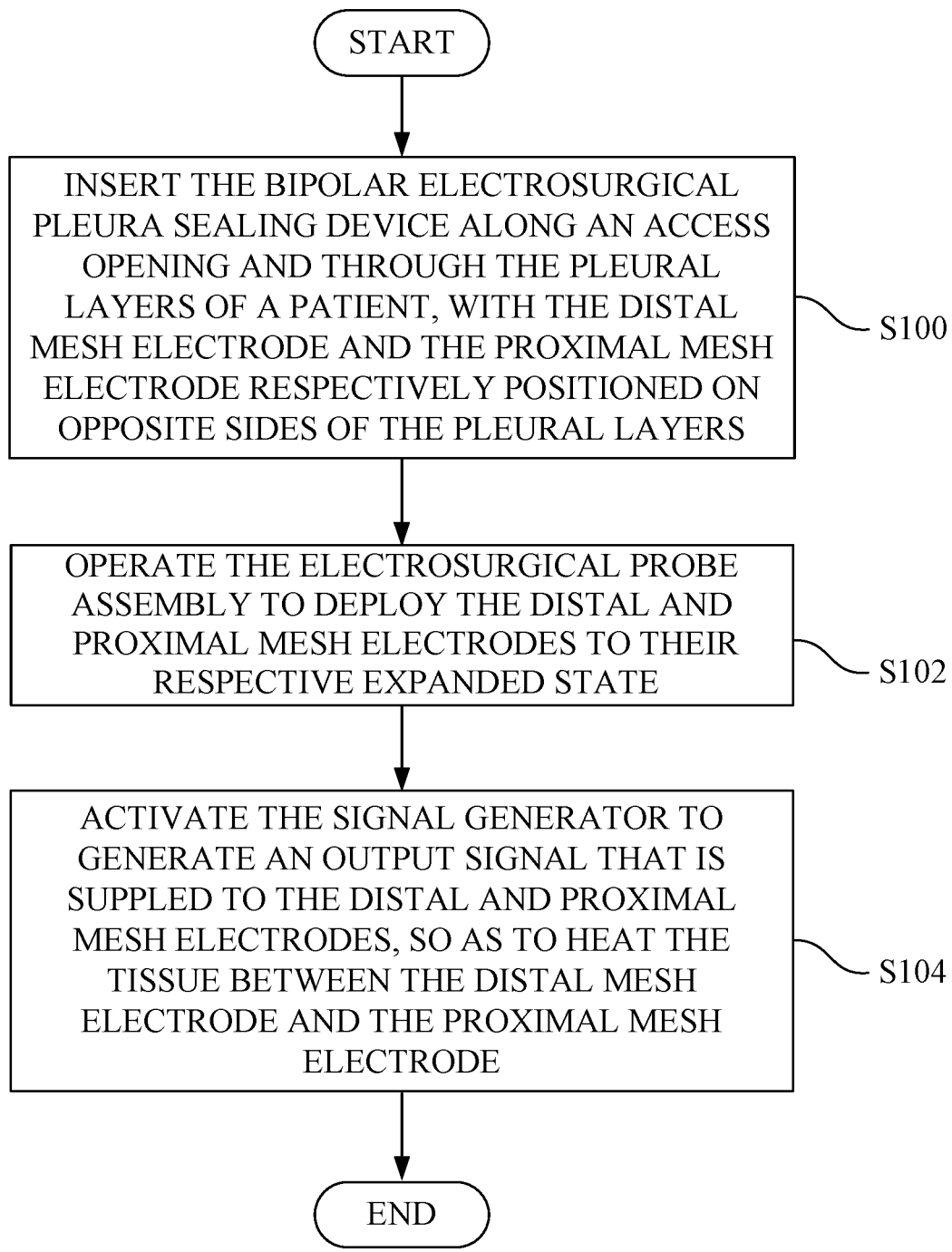
FIG. 10 is a flowchart of a method of using the bipolar electrosurgical pleura sealing system of FIGS. 1 and 2 for use in a lung access procedure to aid in preventing pneumothorax.

FIG. 10 is a flowchart of a method for using bipolar electrosurgical pleura sealing system 10, described above, in a lung access procedure to aid in preventing pneumothorax. The method will be described, and best understood, with further reference to FIGS. 1, 2 and 9.

At step S100, bipolar electrosurgical pleura sealing device 13 is inserted along access opening 54 and through the pleural layers 58, 62 of a subject (see FIG. 9), with distal mesh electrode 16 and proximal mesh electrode 18 respectively positioned on opposite sides of the pleural layers 58, 62.

At step S102, electrosurgical probe assembly 14 is operated to deploy distal mesh electrode 16 to the expanded state 36 and to deploy proximal mesh electrode 18 to the expanded state 40, so as to capture tissue, e.g., pleural layers 58, 62, between distal mesh electrode 16 and proximal mesh electrode 18. For example, distal mesh electrode 16 is moved to the expanded state 36 by an axial movement of at least one of inner stylet 24 and first intermediate cannula 26 of electrosurgical probe assembly 14. Likewise, proximal mesh electrode 18 is moved to the expanded state 40 by an axial movement of at least one of second intermediate cannula 28 and outer cannula 30 of electro surgical probe assembly 14.

At step S104, signal generator 12 is activated to generate an output signal, e.g., a radio frequency signal, that is supplied to distal mesh electrode 16 and proximal mesh electrode 18, so as to heat the tissue, e.g., pleural layers 58, 62, between distal mesh electrode 16 and proximal mesh electrode 18. In the present embodiment, the frequency of the radio frequency signal may be, for example, in a range of 300 kHz and 600 kHz. In one particular example, the frequency of the radio frequency signal may be a frequency of, or about, 492 kHz.

As used herein, "about", and other words of degree are relative modifiers intended to indicate permissible variation from the characteristic so modified.

In the context of frequency, the term "about" means the base frequency plus or minus 2 percent.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bipolar electrosurgical pleura sealing device, comprising:
   an electrosurgical probe assembly having a coaxial arrangement that includes an inner stylet having a distal end portion with a piercing tip, a first intermediate cannula having a first distal end, a second intermediate cannula having a second distal end, and an outer cannula having a third distal end, wherein the inner stylet is electrically insulated from the first intermediate cannula, the first intermediate cannula is electrically insulated from the second intermediate cannula, and the second intermediate cannula is electrically insulated from the outer cannula;
   a first mesh electrode that is connected to and extends between the distal end portion of the inner stylet and the first distal end of the first intermediate cannula, the first mesh electrode configured to have a first extended position that defines a first collapsed state and a first retracted position that defines a first expanded state, wherein the first mesh electrode is configured to move between the first extended position and the first retracted position by an axial movement of at least one of the inner stylet and the first intermediate cannula; and
   a second mesh electrode that is connected to and extends between the second distal end of the second intermediate cannula and the third distal end of the outer cannula, the second mesh electrode configured to have a second extended position that defines a second collapsed state and a second retracted position that defines a second expanded state, wherein the second mesh electrode is configured to move between the second extended position and the second retracted position by an axial movement of at least one of the second intermediate cannula and the outer cannula,
   wherein, when the first mesh electrode is in the first expanded state and the second mesh electrode is in the second expanded state, the first mesh electrode and the second mesh electrode define a tissue compression space therebetween that is adjustable to compress tissue between the first mesh electrode and the second mesh electrode.

2. The bipolar electrosurgical pleura sealing device of claim 1, comprising a first electrical lead connected to the first mesh electrode, and a second electrical lead connected to the second mesh electrode.

3. The bipolar electrosurgical pleura sealing device of claim 1, wherein each of the first intermediate cannula and the second intermediate cannula is made of an electrically non-conductive material.

4. The bipolar electrosurgical pleura sealing device of claim 1, wherein the first intermediate cannula has a first insulation coating, and the second intermediate cannula has a second insulation coating.

5. The bipolar electrosurgical pleura sealing device of claim 4, wherein each of the first insulation coating and the second insulation coating includes at least one of ceramic, rubber, and plastic.

6. A bipolar electrosurgical pleura sealing system, comprising:
   a signal generator having a first electrical port and a second electrical port, the signal generator configured to generate an output signal;
   an electrosurgical probe assembly having a coaxial arrangement that includes an inner stylet having a distal end portion with a piercing tip, a first intermediate cannula having a first distal end, a second intermediate cannula having a second distal end, and an outer cannula having a third distal end, wherein the inner stylet is electrically insulated from the first intermediate cannula, the first intermediate cannula is electrically insulated from the second intermediate cannula, and the second intermediate cannula is electrically insulated from the outer cannula;
   a first mesh electrode coupled in electrical communication with the first electrical port of the signal generator, wherein the first mesh electrode is connected to and extends between the distal end portion of the inner stylet and the first distal end of the first intermediate cannula, the first mesh electrode configured to have a first extended position that defines a first collapsed state and a first retracted position that defines a first expanded state, wherein the first mesh electrode is configured to move between the first extended position and the first retracted position by an axial movement of at least one of the inner stylet and the first intermediate cannula; and
   a second mesh electrode coupled in electrical communication with the second electrical port of the signal generator, wherein the second mesh electrode is connected to and extends between the second distal end of the second intermediate cannula and the third distal end of the outer cannula, the second mesh electrode configured to have a second extended position that defines a second collapsed state and a second retracted position that defines a second expanded state, wherein the second mesh electrode is configured to move between the second extended position and the second retracted position by an axial movement of at least one of the second intermediate cannula and the outer cannula,
   wherein, when the first mesh electrode is in the first expanded state and the second mesh electrode is in the second expanded state, the first mesh electrode and the second mesh electrode define a tissue compression space therebetween that is adjustable to compress tissue between the first mesh electrode and the second mesh electrode.

7. The bipolar electrosurgical pleura sealing system of claim 6, comprising:
   a first electrical lead that is electrically coupled to each of the first mesh electrode and the first electrical port of the signal generator; and
   a second electrical lead that is electrically coupled to each of the second mesh electrode and the second electrical port of the signal generator.

8. The bipolar electrosurgical pleura sealing system of claim 6, wherein the signal generator is a radio frequency signal generator and the output signal is a radio frequency signal.

9. The bipolar electrosurgical pleura sealing system of claim 8, wherein one of the first mesh electrode and the second mesh electrode is a primary electrode and the other of the first mesh electrode and the second mesh electrode is a return electrode, and wherein the radio frequency signal travels through the tissue captured between the first mesh electrode in the first expanded state and the second mesh electrode in the second expanded state to heat the tissue.

10. The bipolar electrosurgical pleura sealing system of claim 8, wherein the radio frequency signal has a frequency in a range of 300 kHz and 600 kHz.

11. The bipolar electrosurgical pleura sealing system of claim 8, wherein the radio frequency signal has a frequency of, or about, 492 kHz.

12. The bipolar electrosurgical pleura sealing system of claim 8, wherein the radio frequency signal generator is configured to supply the radio frequency signal to the electrosurgical probe assembly when the first mesh electrode is in the first expanded state and the second mesh electrode is in the second expanded state.

13. The bipolar electrosurgical pleura sealing system of claim 6, wherein each of the first intermediate cannula and the second intermediate cannula is made of an electrically non-conductive material.

14. The bipolar electrosurgical pleura sealing system of claim 6, wherein the first intermediate cannula has a first insulation coating, and the second intermediate cannula has a second insulation coating.

15. The bipolar electrosurgical pleura sealing system of claim 14, wherein each of the first insulation coating and the second insulation coating includes at least one of ceramic, rubber, and plastic.

16. A method of operating a bipolar electrosurgical pleura sealing system, comprising:
providing a bipolar electrosurgical pleura sealing device that has an electrosurgical probe assembly coupled to a first mesh electrode and a second mesh electrode, each of the first mesh electrode and the second mesh electrode being coupled in electrical communication with a signal generator, the first mesh electrode being movable between a first extended position that defines a first collapsed state and a first retracted position that defines a first expanded state, and the second mesh electrode being movable between a second extended position that defines a second collapsed state and a second retracted position that defines a second expanded state;
inserting the bipolar electrosurgical pleura sealing device along an access path in a subject;
operating the electrosurgical probe assembly to deploy the first mesh electrode to the first expanded state and to deploy the second mesh electrode to the second expanded state, the first mesh electrode and the second mesh electrode defining a space between that is adjusted by movement of the first mesh electrode and the second mesh electrode relative to one another to capture and hold tissue between the first mesh electrode and the second mesh electrode; and
activating the signal generator to generate an output signal that energizes the first mesh electrode and the second mesh electrode to heat the tissue between the first mesh electrode and the second mesh electrode.

17. The method of claim 16, wherein the signal generator is a radio frequency signal generator and the output signal is a radio frequency signal, the method further comprising supplying the radio frequency signal between the first mesh electrode and the second mesh electrode through the tissue.

18. The method of claim 17, wherein a frequency of the radio frequency signal is in a range of 300 kHz and 600 kHz.

19. The method of claim 17, wherein a frequency of the radio frequency signal is of, or about, 492 kHz.

20. The method of claim 16, wherein:
the electrosurgical probe assembly has a coaxial arrangement that includes an inner stylet having a distal end portion with a piercing tip, a first intermediate cannula having a first distal end, a second intermediate cannula having a second distal end, and an outer cannula having a third distal end, wherein the inner stylet is electrically insulated from the first intermediate cannula, the first intermediate cannula is electrically insulated from the second intermediate cannula, and the second intermediate cannula is electrically insulated from the outer cannula,
the first mesh electrode is connected to and extends between the distal end portion of the inner stylet and the first distal end of the first intermediate cannula, and
the second mesh electrode is connected to and extends between the second distal end of the second intermediate cannula and the third distal end of the outer cannula.

\* \* \* \* \*